United States Patent [19]

LeMay

[11] 4,035,651
[45] July 12, 1977

[54] RADIOGRAPHY DEVICE WITH CIRCUITRY TO CORRECT FOR PHOTODETECTOR SENSITIVITY

[75] Inventor: Christopher Archibald Gordon LeMay, Osterley, England

[73] Assignee: E M I Limited, Hayes, England

[21] Appl. No.: 543,364

[22] Filed: Jan. 23, 1975

[30] Foreign Application Priority Data

Jan. 31, 1974 United Kingdom ............... 4563/74

[51] Int. Cl.² ......................................... G01N 23/04
[52] U.S. Cl. ........................ 250/445 T; 250/358 R
[58] Field of Search ............ 250/363 S, 362, 445 T, 250/358 R

[56] References Cited

U.S. PATENT DOCUMENTS

| | | | |
|---|---|---|---|
| 3,778,614 | 12/1973 | Hounsfield | 250/362 |
| 3,780,290 | 12/1973 | Hoffer | 250/363 S |
| 3,784,820 | 1/1974 | Miraldi | 250/362 |
| 3,808,440 | 4/1974 | Petit-Clerc | 250/363 S |
| 3,852,611 | 12/1974 | Cesar | 250/445 T |
| 3,940,625 | 2/1976 | Hounsfield | 250/445 T |

Primary Examiner—Alfred E. Smith
Assistant Examiner—David K. Moore
Attorney, Agent, or Firm—Fleit & Jacobson

[57] ABSTRACT

In an apparatus for examining a body by means of penetrating radiation a source is arranged to direct a swath of radiation through the body and a plurality of detectors are arranged to receive it thereafter. The source and detectors are arranged to orbit the body to obtain data for use in constructing a distribution of absorption of the radiation for part of the body. To correct for sensitivity variations in the detectors they are arranged to obtain data for radiation, not having passed through the body, from a further standard source at least twice in the orbital movement.

17 Claims, 4 Drawing Figures

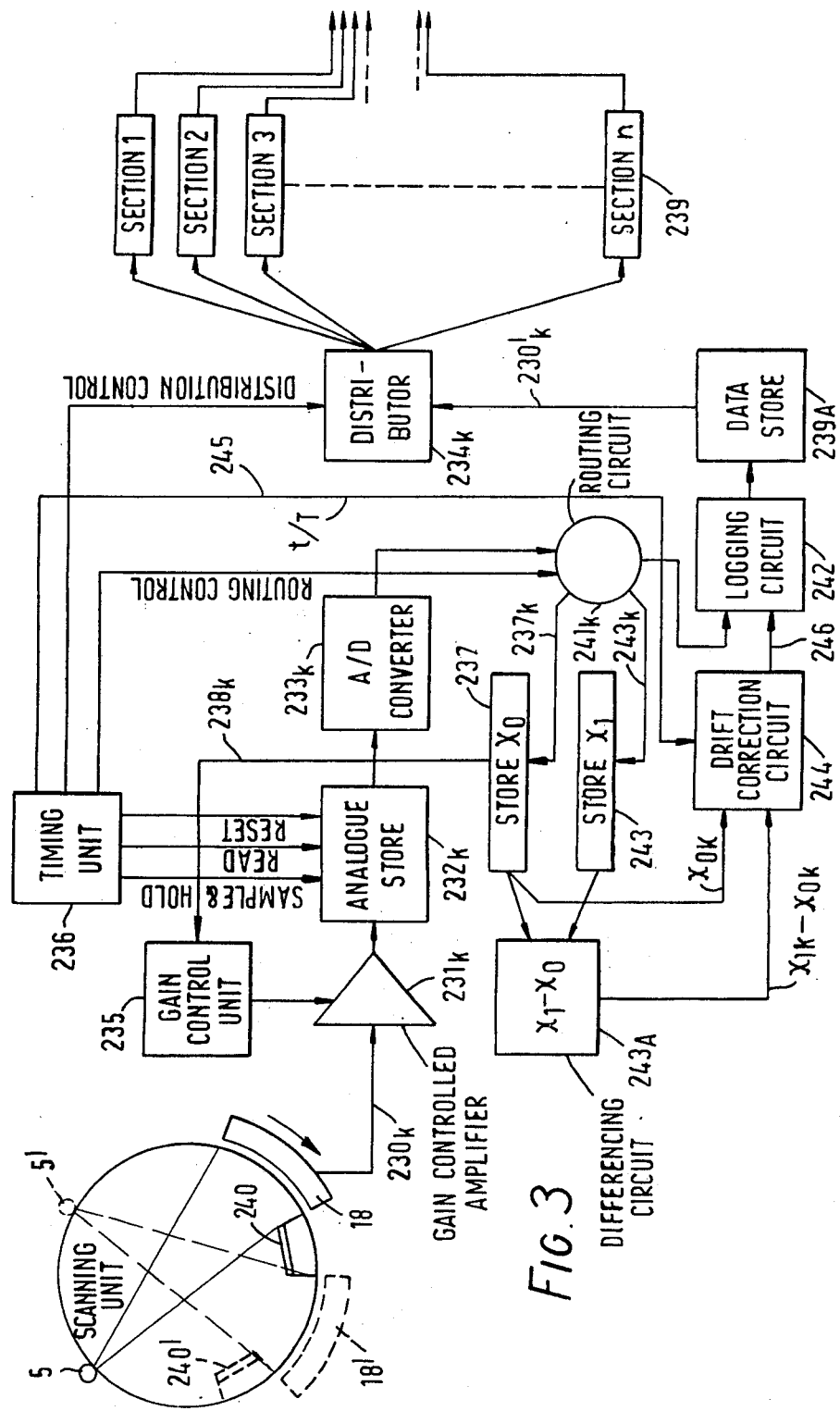

RADIOGRAPHY DEVICE WITH CIRCUITRY TO CORRECT FOR PHOTODETECTOR SENSITIVITY

This invention relates to a method of an apparatus for examining a body by means of radiation such as X or γ radiation.

The method and apparatus according to the invention can be used to assist in the production of radiographs in any convenient form, such as a picture on a cathode ray tube or other image forming device, a photograph of such a picture, or a map of absorption coefficients such as may be produced by a digital computer and on which contours may subsequently be drawn.

In the method of, and apparatus for, examining a body described in U.S. Pat. No. 3,778,614 radiation is directed through part of the body, from an external source, in the form of a pencil beam. A scanning movement is imposed on the beam so that it takes up in turn a large number of differing dispositions, and a detector is used to provide a measure of the absorption of the beam in each such disposition after the beam has passed through the body. So that the beam takes up these various dispositions the source and the detector are reciprocated in a plane and are orbited about an axis normal to the plane. The various dispositions thus lie in a plane through the body over which the distribution of absorption coefficient for the radiation used is derived by processing the beam absorption data provided by the detector. The processing is such that the finally displayed distribution of absorption is the result of successive approximations.

The method and apparatus described in the aforesaid United States Patent has provided to be successful for producing cross-sectional representation of parts of the living body, such as the head.

In order to achieve shorter examination time that can be achieved with this apparatus it has been proposed in the U.S. patent application Ser. No. 532,188 filed 12-12-74 (Hounsfield) and now U.S. Pat. No. 3,999,073 to derive the absorption data signals by directing a sectoral swath of X-rays, emanating from a source, through the body in the plane to be examined, and providing a band of detectors on the other side of the body which measure the radiation transmitted along a set of beam paths within the swath. The sectoral swath subtends an angle sufficient to include the whole region of interest in the plane of the body so that a complete scan of the plane can be effected merely by orbiting the source and the detectors about the body. However when such an arrangement is adopted the absorption data signals derived from the different detectors may include spurious differences due to differential variation in the sensitivities of the various detectors. It is found in practice that such differential variations can occur to a significant degree even in the relatively short time required for scanning a plane.

One object of this invention is to provide for compensating for such spurious differences.

According to one aspect of the invention there is provided an apparatus for examining a body by means of penetrating radiation, such as X- or γ- radiation, including source means arranged to irradiate a region of the body by means of a swath of said radiation, detector means, comprising a plurality of detectors, arranged to determine the intensity of said radiation after passing through the body, means for orbiting the source and detector means about a common axis in and substantially perpendicular to the plane of said swath of radiation, auxiliary source means arranged to irradiate said detectors at at least two spaced positions on the path of said orbital movement with monitoring amounts of radiation, and processing means arranged to utilise further data, received from said detectors and relating to said auxiliary source, to correct data derived from radiation from said first mentioned source means for errors caused by sensitivity variations in said detectors.

According to a further aspect of the invention there is provided a method of examining a body by means of penetrating radiation such as X- or δ -radiation including the steps of irradiating a region of the body by means of a fan shaped spread of radiation, determining the intensity of said radiation after passage through the body, orbiting a source of said radiation and a plurality of detectors about a common axis in and substantially perpendicular to the plane of said fan of radiation, exposing said detectors to further radiation at at least two positions, separated by a predetermined interval, in said orbital movement, processing data representing the intensity of said radiation to derive a reconstruction of the distribution of the absorption of radiation within a part of the body and utilising further data provided by said detectors relating to said further radiation to correct said first mentioned data for errors caused by sensitivity variations in said detectors.

In order that the invention may be clearly understood and readily carried into effect, the same will now be described with reference to the accompanying drawings of which:

FIG. 1a is an enlarged view of a small part of FIG. 1;

FIG. 3 illustrates the operation of the digital computer in compensating drift of sensitivity of the detector means providing the data.

Figure 1:
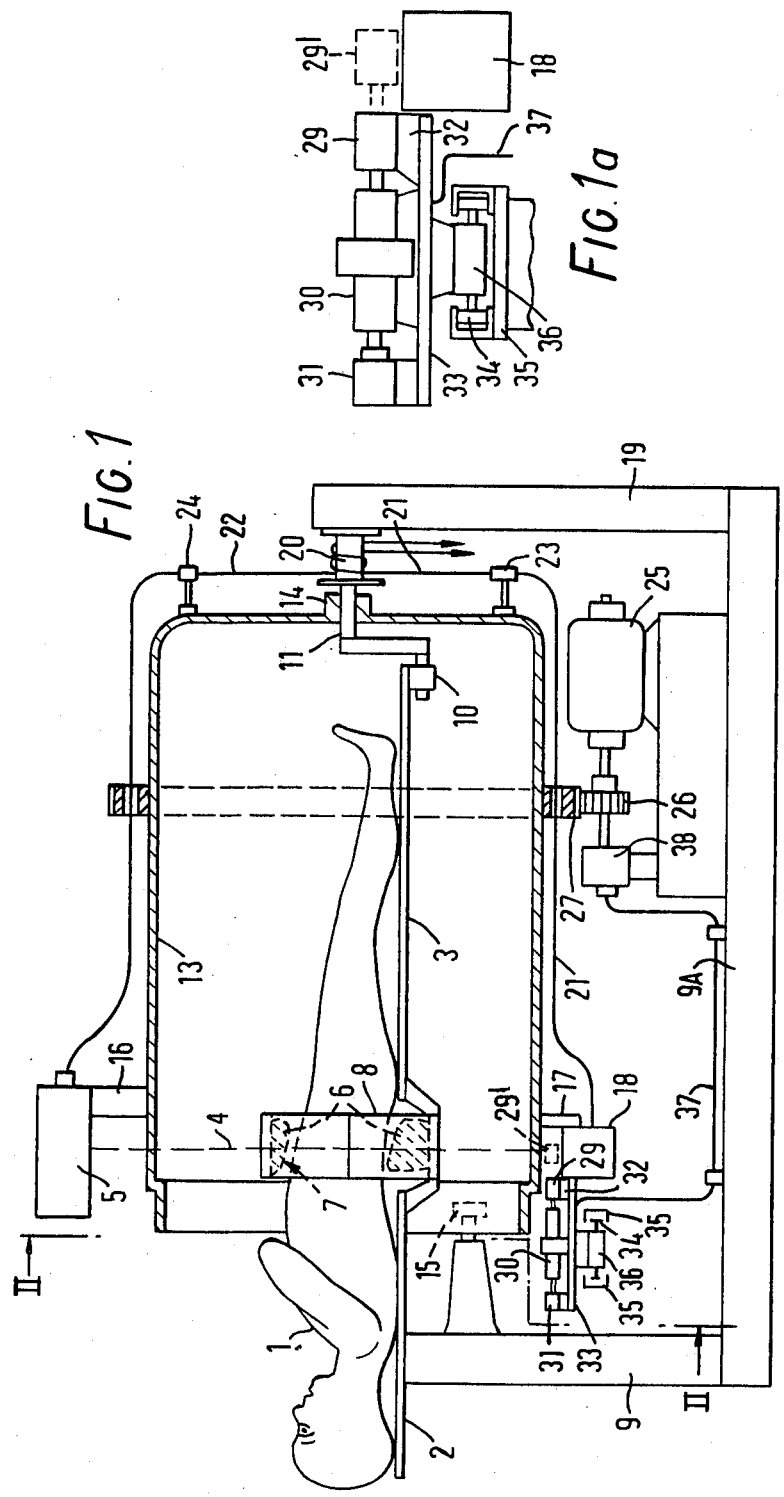
FIG. 1 shows the general layout in side elevation of an apparatus in accordance with the invention.

In FIG. 1 the patient is shown lying on supporting means formed in two parts, 2 and 3 and his body is subject to examination by X-radiation indicated in broken line at 4. This radiation is generated by a source 5 and forms a fan shaped spread in a plane lying at right angles to the plane of the paper. It will be appreciated that the patient supporting means has to be sufficiently long to allow any desired section of the patient's body to be located in the plane of the X-radiation.

In the region of the exploring radiation, the body of the patient is surrounded by a liquid medium, which may be water, and which has an absorption coefficient for the radiation closely similar to that of body tissue. The liquid is shown in the figure at 6 and contained within an envelope, or bag 7. The envelope 7 is positioned within a ring like structure 8 which may be of metal such as duralumin. The ring member 8 is held by retaining means not shown in the figure.

The part 2 of the patient supporting means is supported on an upright 9 forming part of the main frame 9A. The part 3 is supported at its end remote from the ring member 8 by a bearing 10 carried on an axle member 11, which member has an axis about which the orbiting motion of the X-ray source 5 takes place as will be made more clear. The parts 2 and 3 are joined via the ring member 8.

Around the body of the patient when he is located in position in the apparatus there is disposed a surround or frame 13 which is cylindrical along its length having a longitudinal axis which is the axis of the axle member 11. At its end adjacent this latter member it is closed and supported by a bearing 14 which in turn is supported by the member 11. At its other end it is open to allow of positioning of the patient within it, and at this end it is supported on rollers 15 which have suitable fixed bearings. These rollers are such that the surround member 13 is free to rotate on its axis, which as has been indicated in the axis about which the orbiting motion of the X-ray source 5 takes place. The source 5 is mounted on the surround member 13 by means of a support 16. Directly opposite the source 5 there is mounted on the surround member 13 by means of a support 17 a detector system 18 so as to provide radiation absorption data from the body of the patient in the plane of the radiation from the source 5.

The axle member 11 is carried by a support 19 and adjacent the support 19 and surrounding the axle member 11 is a bobbin 20. This last element is fixed to the upright 19 and wound round it are cables 21 and 22 respectively carrying absorption data from the detector means 18 to the processing unit and supplying power from the X-ray source 5. With the orbiting motion of the source and detector means the cables wind on or off the bobbin 20. They are fed to the bobbin via guides 23 and 24 respectively which are carried by the surround member 13. This member may make one or more orbiting revolutions and the cables wrap or unwrap in relation to the bobbin 20 correspondingly. At the bobbin the cables are secured and thence pass to their respective connecting units, namely the data processing unit mentioned, and a power supply unit. The orbiting movement of the member, and with it the source 5 and detector system 18 is effected by a motor 25 via gears 26 and 27, the gear 27 being formed on the surround member 13.

Figure 2:
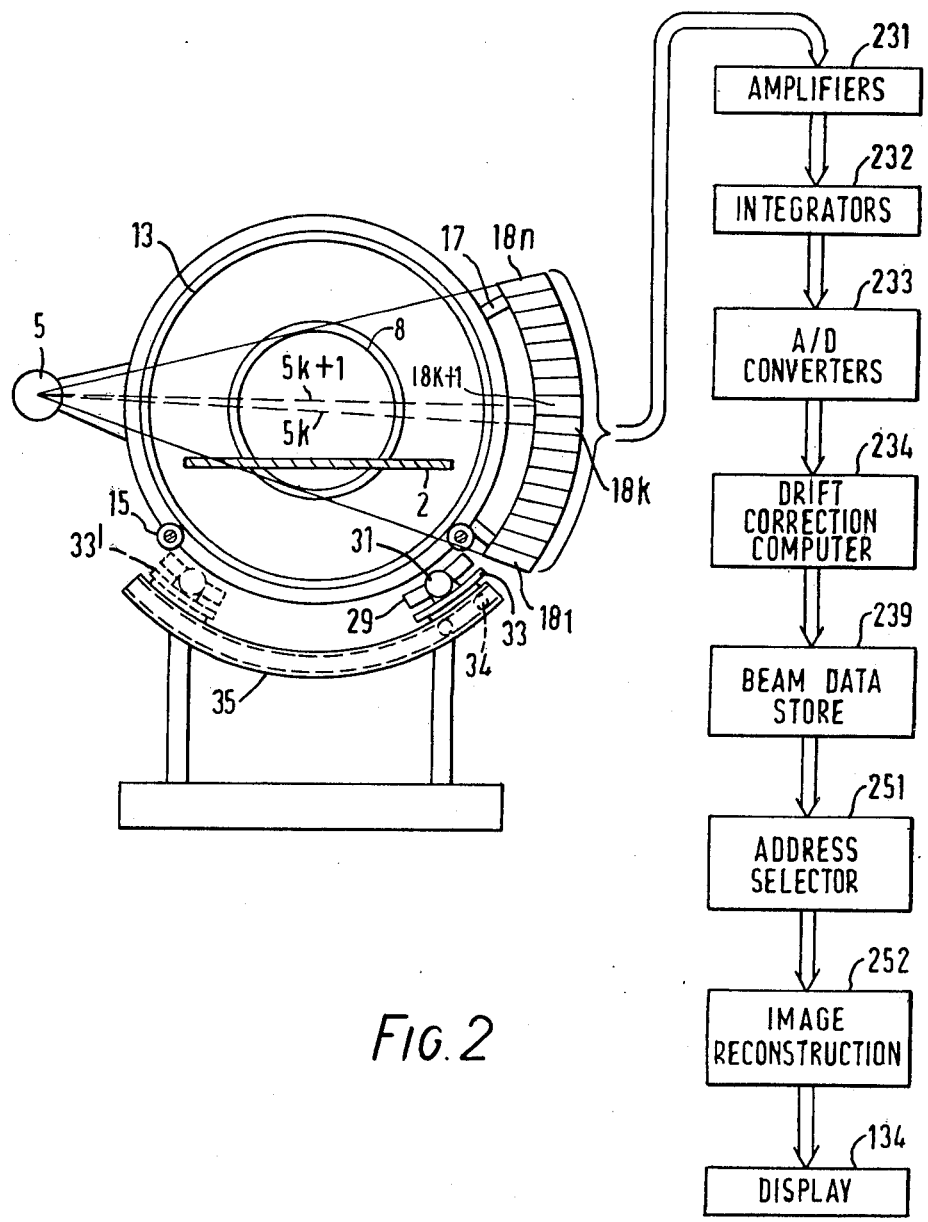
FIG. 2 illustrates the same apparatus in end elevation, looking in the direction of the arrows II—II of FIG. 1, part of the apparatus being angularly displaced from the position in which it is illustrated in FIG. 1.

The apparatus so far described is generally similar to that described in U.S. application Ser. No. 532,188 fied 12-12-74 (Hounsfield). The present invention is concerned with monitoring the detectors included in the detector system which may occur even during the time of one examination. As indicated in FIG. 2, the radiation from the source 5 is collimated to confine it to a sectoral swath which just encompasses the ring member 8, and the detector system comprises a series of individually collimated detectors $18_1 \ldots 18_k \ldots 18_n$, arranged so that each one detects substantially only radiation received along a narrow finger like beam path included in the swath of radiation, two such beam paths being denoted as $5_k$ and $5_{k+1}$ incident respectively on detector $18_k$ and $18_{k+1}$. Each detectors preferably comprises in known manner, a scintillating crystal which emits a light pulse if a quantum of high energy radiation is incident upon it, and a photo-multiplier which converts the light pulse into an electrical pulse. Other forms of detectors may however be used. For the purpose of monitoring the sensitivity of the detectors $18_1 \ldots 18_n$ the apparatus is provided with an auxiliary source of radiation included with a shielded and collimated box 29 which allows radiation to emerge only from the side nearer the detectors 18. The box 29 is carried by a rod housed in the sleeve 30 of a nut and screw mechanism, the nut of the mechanism being driven by a small electric motor 31 (see FIG. 1a). The electric motor can be operated to move the box 29 from the position shown in full lines in FIG. 1 to that shown in dotted lines and denoted as $29^1$. In the full line or "withdrawn" position, the one open side of the box is closed by a radiation shield 32 (FIG. 1a) which substantially prevents any escape of radiation. When the box 29 is moved to the "dotted" line or projecting position it lies in the path of the detectors 18, so that the detectors can move under the box in very close relationship to the open side thereof and receive radiation therefrom. The source of radiation in the box is a γ-ray source, say Americium, emitting an exactly known number of quanta in the time each detector 18 takes to pass the box 29, during normal rotation of the frame member 13. The source, denoted 240 in FIG. 3, extends for the full angular extent of the box 29 as seen in FIG. 2, the object being to make the count received by each detector sufficiently large to reduce to negligable quantities, variations due to statistical fluctuations. The box 24 and the mechanism for selectively projecting or withdrawing it, is supported as seen in FIG. 1a, by a carriage having wheels 34 which run in arcuate rails 35, two of the wheels 34 being driven by an electric motor 36 whereby the carriage may be driven between the position shown in full lines in FIG. 2 and that shown in dotted lines and indicated by reference 33'. Electromagnetic means, not shown, is provided to lock the carriage in each position for predetermined times. The power supply to the electric motors 31 and 36, and the electromagnetic latches is provided by a cable 37 (FIG. 7), which emanates from a cam operated switching timer 38 driven by the electric motor 25. The sequence of operation is as follows.

FIG. 2 shows the position of the apparatus for the start of the examination of a patient. The switch is operated to start the motor 25 which starts the rotation, in clockwise direction as seen in FIG. 2, of the member 13 and with it the source 5 (which is switched off at this time) and the detector system 18. Simultaneously the power to the motor 31 is switched on by the mechanism 38, rapidly causing the box 29, containing the extended source 240 to project into the position to cooperate with the detectors $18_1 \ldots 18_n$. When the last of the detectors $18_n$ has moved past the source 240, the motor 31 is operated by the switching mechanism 38 in reverse sense to withdraw the box 29 and source 240. At the same time the X-ray source is switched on and the radiation from the source 5 is projected through the patient to be received by the detectors $18_1 \ldots 18_n$. The examination continues for one full revolution of the member 13, the source 5 and detector system 18. At a convenient time during this revolution (the actual time being immaterial) the power is switched on by the switching mechanism 38 to the motor 36 to drive the carriage to the dotted position 33' shown in FIG. 2. This puts it in an angular position just ahead of the detector system 18 when the aforesaid examination cycle has been completed. When the cycle has in fact been completed, the switching mechanism 38 switches off the X-ray source 5, and switches on the motor 31 to rapidly project the box 29 and source 240 into position to co-operate with the detectors $18_1 \ldots 18_n$. When the last detector $18_n$ clears the source 240', the box 29 is again withdrawn. Subsequently all parts are returned to their starting positions and the apparatus is switched off.

The current impulse generated by the individual detectors $18_1 \ldots 18_n$ are applied to respective individual amplifiers, represented collectively by the block 231. The output of the individual amplifiers are in turn passed to integrators 232, one for each detector. Each of these integrators, of the well known Miller integrator type, is arranged to integrate the amplified output of the respective detector, say the detector $18_k$ over successive short intervals of time, in this case the time taken for the member 13 to rotate through an angle less than 1°. During this time when the detectors $18_1 \ldots 18_n$ are exposed to radiation from the source 5, the integrator can be regarded as providing an output signal representative of the radiation received from the source 5, and passing through the patient under examination along a single effectively stationary finger like beam path. Each such signal, called a beam data signal and representing the transmittance of a single beam path, is stored as an individual signal, so that during any one examination, many signals are derived from each detector $18_1 \ldots 18_n$. These signals are however likely to be in error if the sensitivity of the detectors 18 should drift during an examination or series of examinations. The integrators operate in the same way during the intervals when the X-ray source 5 is switched off and the detectors are instead receiving radiation from the γ-ray source 240. All the outputs from any one integrator received from the γ-ray source 240 when in the position shown in full lines in FIG. 2 are accumulated in a single address (for a single detector) in a store and the resultant is called a monitoring signal, and similarly when the source 240 occupies the position shown in dotted lines in FIG. 2. Two monitoring signals are thus derived from each detector $18_1 \ldots 18_n$, one before the actual examination of the patient and one after the examination. The beam data signals and the monitoring signals are fed to a drift correction digital computer 234, via analogue to digital converters 233. The computer, as will be described with reference to FIG. 3, operates to correct the beam data signals for drift in the detectors and the corrected beam data signals in digital form, are fed to a beam data store 239. Thence they are applied, in a prearranged order programmed into an address selector 251, to an image reconstruction computer 252 which in response to the beam data signals generates an accurate representation of the variable transmittance, or radiation density, of the cross sectional plane of the patient irradiated by X-rays from the source 5, during the examination cycle. The method by which image reconstruction is carried out is not material to the present invention, but it may be that described in the U.S. Pat. No. 3,924,129 Reference 134 represents a display device for the resultant representation. The parts represented by references 234, 239, 251 and 252 may in practice be constituted by one suitably programmed digital computer.

It is found that if the detectors $18_1 \ldots 18_n$ have differing sensitivities during an examination cycle, or vary in sensitivity during such a cycle, a ring like pattern may appear in the picture which can seriously impair the accuracy of the image reconstruction. In order that such patterns shall not be obvious the detector sensitivities are effectively determined at least twice for each orbital scan, preferably both immediately before and immediately after the scan. It is then possible to make initial adjustment of the various amplifier gains, namely the gain of each such amplifier of 231, so that the various initial sensitivities are corrected, and by checking the sensitivities at the end of the scan such drifts as may have occurred during the scan may be allowed for assuming some approximate law of drift, for example a linear law.

FIG. 3 illustrates the operation of the drift correction computer for a single detector channel, say that of detector $18_k$. Exactly the same procedure is carried out for all other detector channels. The conductor $230_k$ feeds the output of the detector $18_k$ to the amplifier $231_k$, the gain of which is controlled by a gain control unit 235. The output of amplifier $231_k$ is applied to an analogue store $232_k$. This store is in fact the Miller Integrator referred to before. The operations of the Miller integrator or store $232_k$ are controlled by a timing unit 236 which is synchronised in known manner with the operation of the apparatus shown in FIG. 1. The output of the store is converted to digital form by an analogue digital converter $233_k$. In FIG. 3 the detector system 18 is shown in full line just about to be exposed to the X-radiation of the extended auxiliary source 240, the source of exploring X-rays not as yet being switched into operation.

As the detectors of the unit 18 become exposed to the source 240 each receives a photon count of the order of 10 times or more the count they experience on average per beam absorption measurement during body exploration. They are thus subject to a sensitivity check of accuracy appreciably greater than that of normal exploring beam measurement. It will be appreciated that the source need not be of extended form provided it is of sufficient intensity to achieve such a count.

The output of the analogue-to-digital converter circuit $233_k$ is applied to a routing circuit $241_k$ which is controlled by the timing unit 236, and with the approach in the orbital motion of the detector system 18 to the auxiliary source 240 the output of the analogue-digital converter $233_k$ is routed to a store 237 which has available one address relative to each of the various detectors. The stored magnitudes stored at these addresses represent the accumulated counts of the various detectors as they become exposed to the extended source 240.

The monitoring signal stored in address $k$ of store 237 is applied to the unit 235 to adjust the gain of the corresponding amplifier $231_k$, before the X-source is switched on the detectors $18_1 \ldots 18_n$ become exposed to radiation therefrom. Since this gain adjustment is effected for all amplifiers differences in sensitivity of the various detectors are compensated for before the examination commences.

When all addresses in the store 237 are filled with check values, the exploring X-ray source 5 is switched on to explore the cross section of the body under examination, and the output of the converter circuit $233_k$, converting now beam data signals, is routed via the circuit $241_k$ and after logarithmic conversion by a logging circuit 242 to an ante-store 239A which stores individually in logarithmic form the counts for each detector for each of its positions in the orbital scan. Since the orbital scan is continuous such positions are each a mean position during a count.

The detector system 18 as shown in dotted outline at 18′ is to be regarded as located in the position it occupies on switching on the exploring X-ray source at 5, which position also is the position to which it returns after one complete revolution of exploring scan.

With the commencement of this revolution the auxiliary source 240 is withdrawn, as previously explained, and as the revolution nears completion the source 240 is repositioned as shown in dotted outline at 240', such that with continued orbital motion after the completion of the exploratory revolution the detectors again become exposed in sequence as before its radiations. The outputs of such converter circuits as $233_k$ are now no longer routed to the data source 239A but rather to addresses of a store 243, as, before the exploratory scan, they were routed to store 237. Thus the output of circuit $233_k$ is routed by routing circuit $241_k$ and conductor $243_k$, to a respective address of store 243. Comparison of the stored magnitudes held in store 243 with those held in store 237 gives, address for address, the change in sensitivity of the corresponding detector in the course of the exploratory revolution. Having made this comparison for each detector and assuming a law of drift, for example linear, the outputs of each detector in all its exploratory positions can be corrected in retrospect and the output as stored in the data store 239A modified correspondingly.

Thus when the detectors of the detecting means 18 have again been exposed to the auxiliary source and all the data thereby deriving stored in store 243, the data stored in ante-store 239A is corrected with respect to the different detectors in turn. Taking as typical the data stored in ante-store 239A for the $k$ th detector, this data is corrected for each position of the detector in the course of the exploratory scan, having regard to the time $t$ relevant to this position and to the sensitivity check values $x_{0k}$ and $x_{1k}$ stored, at address $k$, respectively in stores 237 and 243 relative to the exposures of the $k$ th detector to the source 240 before and after the exploratory scan. The time $t$ is taken as the time elapsed from the deriving and storing of the check value $x_{0k}$.

To correct the store value in the ante-store 239A at the position in question the check values $x_{0k}$ and $x_{1k}$ are withdrawn respectively from store and applied to a differencing circuit 243A to form the difference $x_{1k} - x_{0k}$. This difference is applied by the circuit 243A to a drift correction circuit 244 to which also is applied separately from store 237 the check value $x_{0k}$. The timing unit 236 also applies separately and via conductor 245 a signal to the drift correction circuit 244, this signal having the value $t/T$, in which T is the time elapsed between the deriving and storing of any such check value as $x_{0k}$ and the deriving and storing of the corresponding value $x_{1k}$. The drift correction circuit 244 operates to produce an output signal on conductor 246 of value $$1 + \frac{x_{1k} - x_{0k}}{x_{0k}} \cdot \frac{t}{T}$$

making use of known digital computer operations to do this. The output signal from circuit 244 is applied via conductor 246 to the logging circuit 242, the output from which is transferred subtractively to the data store 239 to correct the respective stored value for the $k$ th detector by a linear correction, that is to say assuming a linear law of drift on the part of the detector. It will be understood that the drift is such as occurs either in the scintillation crystal concerned, or the associated photomultiplier, or both.

The procedure described is also performed in relation to all other addresses in ante-store 239A corresponding to all other detectors of the detector means 18 and the positions which these detectors occupy in the course of exploratory scan.

It will be realized that the whole cycle of events outlined may be repeated in a second cycle. Whether the apparatus is based on one or more than one cycle operation, the data stored in ante-store 239A is distributed, when complete, by distributors of which $234_k$ is typical to the sections 1, 2, 3, ... n of store 239. The distributor $234_k$ is controlled by the timing circuit 236. Data drawn from ante-store 239A to be applied to distributor $234_k$ is all that data relative to detector $k$ of means 18 and is fed from the addresses of ante-store 239A holding this date via conductor $230_k$.

Many modifications may be made to the apparatus described.

Many of the components and circuits illustrated in the drawing are merely shown diagrammatically because they are in the practical apparatus provided by a suitably programmed digital computer. Much of the timing is predicted on the geometry and speed of operation of the apparatus, so that the timing information provided by the timing unit is preprogrammed in the computer.

It is to be understood that the invention is not limited in its application to the particular arrangement described for deriving the beam absorption data signals. The invention is applicable to any arrangement for deriving the necessary absorption data signals.

As one example the invention is used in the type of medical radiology machines sometimes referred to as CAT scanners, in which X-radiation travels along a substantially planar slice through the patient. The X-ray source orbits around the patient so as to send radiation along a number of directions which are at different angles to each other but are all in the slice. The intensity of the radiation emerging from the slice is measured along each of a number of pencil-thin beam paths such that any point in the slice is traversed by a great number of such beam paths. The resulting measurements are processed, for example, as described in U.S. Pat. Nos. 3,778,614 and 3,924,129, to generate a picture in which each point has a brightness corresponding to the X-radiation respone characteristics of the correspondingly positioned point in the slice. The picture looks similar to what would be seen if the patient were cut in two along the slice and one looked at the resulting cross section of the body.

For a good picture of the examined slice, the radiation detectors must be both sensitive and accurate. However, the detectors are often operated near the limits of their capabilities, in order to minimize radiation dosage to the patient and minimize the time for an examination, and as a result two types of detector errors may become significant; drift errors and differential sensitivity errors. Drift errors are due to changes in the sensitivity of a detector in the course of the examination of a patient, and differential sensitivity errors are due to differences between the individual sensitivities of the several detectors which simultaneously detect radiation along several different beam paths.

In machines which combine lateral and orbiting scanning motion of the X-ray source it may be possible to check the sensitivity of the detectors at certain convenient positions of the lateral scan and to make appropriate corrections. However, in machines which use only orbital scanning (or orbital scanning and a possible limited extent of lateral scanning) this solution cannot be used to take into account the drift and differential sensitivity of the detectors, and one important aspect of the invention described above is directed to solving problems of this type. One example of the solution provided by this invention is to test the sensitivity of each detector with an auxiliary radiation source during an examination of a patient, e.g., just before and just after the examination with X-radiation, and to use the checks to correct both drift and differential sensitivity of the detectors. More specifically, just before an examination with X-radiation (before the X-ray source is turned on but after the orbital scan has started) on Americium source of gamma radiation irradiates the detectors as they move in their orbiting motion, and each detector receives a known, identical amount of radiation from the Americium source. The amount of radiation applied to each detector for this checking step is about 10 times the radiation it would typically receive along an individual beam path during the examination of the patient with X-radiation, so that the statistical noise due to the source properties is significantly reduced. After each detector has received radiation from the Americium source and has provided a corresponding test measurement signal, the amplifiers that amplify the signal from each detector are adjusted to make the signals equal, thus correcting for differential sensitivity as between the individual detectors. The Americium source is then moved to its recessed position, the X-ray source is turned on as the detectors continue in their orbital motion, and the orbital motion continues until the examination of the slice wit X-radiation is completed. At that time the X-ray source is turned off, while the orbital motion of the detectors continues, and the detectors are again exposed to radiation from the Americium source, which has meanwhile been moved to its testing position. The sensitivity of each detector is again tested, and the difference between the sensitivity of a detector before and after the X-radiation examination is a measure of the end points of the drift of that detector during the examination. This information is used to correct all readings taken by that detector during the examination in accordance with some assumption of how the sensitivity of the detector has varied between the two known end points (one possible assumption is that the variation has been linear). Thus, in accordance with this aspect of the invention the sensitivity of each detector is tested just before and just after the X-radiation examination, and the resulting signals are used to correct both for drift in the sensitivity of each detector and for differences between the sensitivities of the individual detectors.

What I claim is:

1. An apparatus for examining a body by means of penetrating radiation, such as X- or γ- radiation, including source means arranged to irradiate a region of the body by means of a swath of said radiation, detector means, comprising a plurality of detectors, arranged to determine the intensity of said radiation after passing through the body, means for orbiting the source and detector means about a common axis in and substantially perpendicular to the plane of said swath of radiation, auxiliary source means arranged to irradiate said detectors at at least two spaced positions in the path of said orbital movement with monitoring amounts of radiation, and processing means arranged to utilise further data, received from said detectors and relating to said auxiliary source, to correct data derived from radiation from said first mentioned source means for errors caused by sensitivity variations in said detectors.

2. An apparatus according to claim 1 wherein said two positions are the start and end of the orbital movement.

3. An apparatus according to claim 1 wherein said processing means is arranged to correct each determination of the intensity of radiation received by the detectors from said first source by a factor related to the change in the measured intensity of radiation from said auxiliary source, during said orbital movement, and the elapsed time between the start of said movement and said determination.

4. An apparatus according to claim 1 wherein the character of said auxiliary source is such that each detector receives radiation, during a determination of the intensity of radiation from said auxiliary source, substantially an order of magnitude greater than that received during a determination of the intensity of radiation from said first source.

5. An apparatus according to claim 1 wherein said auxiliary source comprises Americium.

6. Apparatus according to claim 1 in which said auxiliary source is arranged to lie in close proximity to said detectors at said positions and including means for shielding the auxiliary source at other positions.

7. A method of examining a body by means of penetrating radiation such as X- or γ- radiation including the steps of irradiating a region of the body by means of a fan shaped spread of radiation, determining the intensity of said radiation after passage through the body, orbiting a source of said radiation and a plurality of detectors about a common axis in and substantially perpendicular to the plane of said fan of radiation, exposing said detectors to further radiation in at least two positions, separated by a predetermined interval, in said orbital movement, processing data representing the intensity of said radiation to derive a reconstruction of the distribution of the absorption of radiation within a part of the body and utilising further data provided by said detectors relating to said further radiation to correct said first mentioned data for errors caused by sensitivity variations in said detectors.

8. A medical radiology device comprising:
means defining a patient position and means disposed outside the patient position for generating a swath of penetrating radiation which is within a thin transverse region of the patient position, said swath travelling along said region and emerging from the patient position after being modulated by the matter through which it has travelled within the region;
means for orbiting the generating means around an axis transverse to the region to cause said swath of radiation to travel within said region along a plurality of successive directions which are at an angle to each other;
means for detecting the radiation emerging from the patient position in the course of said orbiting of the generating means, said detecting means comprising a plurality of detection devices having individual measurement characteristics and means for measuring with said detection devices the radiation along a plurality of different linear paths through the region and for providing corresponding measurement signals indicative of the radiation received along said paths and for successively measuring with said detection devices the radiation along successive pluralities of different paths through the region and for providing corresponding successive pluralities of measurement signals;

means for testing the measurement characteristics of the detection devices at times references to said orbiting of the generating means to provide corresponding testing signals indicative of the measurement characteristics of the detection devices related to said times;

means for correcting the measurement signals in accordance with the testing signals to derive corrected measurement signals determined both by the measurement signals indicative of the radiation received along said linear paths and by the lasting signals indicative of the measurement characteristics of the detection devices, and means for processing the corrected measurement signals to construct a representation of the distribution within said thin transverse region of the radiation response characteristics of the matter therein which modulate the radiation travelling along the region.

9. A medical radiology device as in claim 8 wherein the measurement characteristics of the detection devices include sensitivity characteristics and the testing means includes means for testing the sensitivity characteristics of each detection device at least twice during a time interval related to said orbiting of the generating means and for including in said testing signals a calculated indication of the sensitivity characteristics of each detection device at the times measurement signals are obtained with said detection device.

10. A medical radiology device as in claim 9 wherein the testing means include means for correcting the measuring means for differences between the sensitivity characteristics of the individual detection devices.

11. A medical radiology device as in claim 10 wherein the testing means include an auxiliary source of radiation having a recessed position in which it does not irradiate the detection devices and a testing position in which it irradiates the detection devices with known amounts of radiation and means for placing the auxiliary source in its testing position at least twice within said time interval related to the orbiting of the generating means.

12. A medical radiology device as in claim 11 wherein the auxiliary source is a source of gamma radiation and the testing means include means for preventing the irradiation of a detection device with radiation from the generating means while the detection device is being irradiated with radiation from the auxiliary source.

13. A medical radiology device as in claim 12 wherein the amount of radiation received by a detection device while the auxiliary source is in its testing position is about an order of magnitude greater than the typical amount of radiation from the generating means measured with the detecting device along one of said linear paths.

14. A medical radiology device as in claim 8 wherein the measurement characteristics of each detection device include sensitivity characteristics and the testing means include means for testing the sensitivity characteristics of each detection device at least prior to said orbiting of the generating means and for including in said testing signal an indication of differences in sensitivity characteristics as between the detection devices.

15. A medical radiology examination method comprising the steps of:

generating a swath of penetrating radiation which travels within a substantially planar region of space intersecting a patient position and emerges from the patient position after suffering absorption determined by the matter within the region through which it has travelled;

orbiting the swath around an axis transverse to the plane of the region to thereby direct the swath along a plurality of successive directions at an angle to each other;

detecting the radiation emerging from the patient position in the course of said orbiting with a plurality of detection devices having individual measurement characteristics and measuring with said detection devices the radiation along a plurality of different substantially linear paths through the region to derive successive sets of measurement signals, each set comprising measurement signals for each of the substantially linear paths within the swath of radiation along one of said successive directions thereof;

testing the measurement characteristics of the detection devices at times referenced to the orbiting of the swath of radiation to provide corresponding testing signals indicative of the measurement characteristics of the detection devices related to said times;

correcting the measurement signals in accordance with the testing signal to derive corrected measurement signals determined both by the measurement signals indicative of the radiation received along said linear paths and by the testing signal indicative of the measurement characteristics of the detection devices; and processing the corrected measurement signals to construct a representation of the distribution within said substantially planar region of the radiation absorption characteristics of the matter therein.

16. A method as in claim 15 wherein the measurement characteristics of the detection devices include sensitivity characteristics and the testing step includes the substep of testing the sensitivity characteristics of each detection device at least twice during a time interval related to said orbiting of the swath of radiation and including in said testing signals a calculated indication of the sensitivity characteristics of each detection device at the times measurement signals are obtained from said detection device.

17. A method as in claim 15 wherein the step of correcting the measurement signals in accordance with the testing signals includes the substep of correcting the measurement signals for differences between the sensitivity characteristics of the individual detection devices.

* * * * *